United States Patent [19]

Piasio et al.

[11] Patent Number: 5,384,262

[45] Date of Patent: Jan. 24, 1995

[54] QUANTITATIVE IMMUNOASSAY FOR VOLATILE ORGANIC COMPOUNDS

[75] Inventors: Roger N. Piasio, Cumberland Foreside; Leslie Latt, Litchfield, both of Me.

[73] Assignee: Quantix Systems, L.P., Cinnaminson, N.J.

[21] Appl. No.: 68,268

[22] Filed: May 28, 1993

Related U.S. Application Data

[63] Continuation of Ser. No. 619,956, Nov. 30, 1990, abandoned.

[51] Int. Cl.$^6$ .................. G01N 33/543; G01N 33/552
[52] U.S. Cl. ...................................... 436/518; 422/83; 422/88; 435/7.92; 435/7.93; 436/139; 436/140; 436/527; 436/805; 436/810
[58] Field of Search ............... 436/139, 140, 518, 547, 436/548, 805, 810, 527; 422/83, 86, 88; 435/7.9, 7.92, 7.93, 7.94

[56] References Cited

U.S. PATENT DOCUMENTS

| | | | |
|---|---|---|---|
| 4,022,878 | 5/1977 | Gross | 436/542 |
| 4,135,884 | 1/1979 | Shen | 436/810 |
| 4,197,287 | 4/1980 | Piasio et al. | 436/810 |
| 4,210,418 | 7/1980 | Brown et al. | 422/58 |
| 4,305,924 | 12/1981 | Piasio et al. | 436/810 |
| 4,383,984 | 5/1983 | Karol et al. | 436/543 |
| 4,758,521 | 7/1988 | Lushbaugh et al. | 422/60 |

OTHER PUBLICATIONS

Petrucci, *General Chemistry*, 4th ed., New York, Macmillan Publishing Company, 1985, p. 291.

*Primary Examiner*—Toni R. Scheiner
*Assistant Examiner*—Christopher L. Chin
*Attorney, Agent, or Firm*—Pennie & Edmonds

[57] ABSTRACT

The invention pertains to an immunoassay method for determining the presence of volatile organic compounds in aqueous, soil and air samples by simultaneously collecting and testing a sample volume suspected to contain such organic compounds. As a major problem in the assay of such materials is their rapid evaporation, the present immunoassay is specifically designed to eliminate or minimize the evaporation of the volatile organic analyte during sample handling as well as during the assay process itself. The immunoassay method is based on an assay vessel which has a lower portion, in which the immunoassay actually takes place, and an inert upper portion, which can hold a sufficiently large volume of sample to prevent or minimize evaporation of the organic compound from the smaller volume in the lower portion. The assay is performed by: (1) coating the vessel's lower portion with an antibody specific for the organic analyte; (2) adding the sample to the vessel, wherein the volume of the sample added is between about two to about thirty times the volume of the vessel's lower portion; (3) adding a conjugate between a detectable label and an organic compound for which the antibody is specific; (4) allowing the organic analyte and the added conjugate to compete for binding to the immobilized antibody; and (5) detecting the binding of the detectable label to the immobilized antibody. In another embodiment of the immunoassay, the lower portion of the vessel has inserted therein a solid phase device whose surface is coated with an immobilized antibody specific for the organic analyte.

15 Claims, 1 Drawing Sheet

FIG. 1

QUANTITATIVE IMMUNOASSAY FOR VOLATILE ORGANIC COMPOUNDS

This is a continuation of application Ser. No. 07/619,956, filed Nov. 30, 1990 now abandoned.

This U.S. patent application is related to U.S. Disclosure Document Number 257504 filed Jul. 12, 1990.

BACKGROUND OF THE INVENTION

The growing emphasis on the state of the environment requires the development of accurate, inexpensive testing methods to detect organic contaminants in soils and water. The effective pollution management of our lakes, other waterways, subsoils and the subterranean water table demands regular and stringent testing. The effectiveness of such testing is enhanced when the tests are simple, inexpensive, can be operated on site and give a rapid result. In this way, the progress of the toxic clean-up from the waterway can be monitored to see if clean-up efforts are meeting existing state or federal guidelines. Very often soil assays must be made before land sales can be completed if the presence of a contaminant once existed on the site or suspected to be present. The detection of the adverse effects from leaking underground storage tanks can be enhanced if convenient tests can be routinely run on soil and water samples taken directly from near the buried storage tanks. The extent to which a toxic spill has penetrated and thus contaminated the subsoil and/or the groundwater can be more effectively determined, assayed and monitored if the subsoil and/or the groundwater can be collected, sampled and tested directly on-site.

Further, the safety of workers in enclosed working facilities which handle potentially harmful organic compounds could be enhanced if simple testing kits were available to test routinely and accurately for the presence of contaminants in the air or water being consumed by the work force. For example, factory air could easily be bubbled through an aqueous solution which in turn could be tested for the presence of the harmful organic compounds. Alternatively, absorptive charcoal badges as are known in the art and used in the workforce, could be worn by the workers, collected after a specified period, treated with suitable extraction liquid and assayed.

However, it has been difficult accurately to assess the presence, especially on a quantitative basis, of certain volatile non-polar organic compounds such as, for example, benzene, toluene, xylene, perchloroethylene and trichloroethylene, that have limited solubility in polar solvents e.g., in water. Some organic compounds are so volatile that even short delays in testing a sample can result in their evaporating from the sample completely, or at very least, sufficiently to significantly alter the true value of the actual contaminant concentration in a particular environment. This problem is exacerbated when the contaminant being tested for is non-polar and only minimally soluble in common polar solvents such as water.

Water is an important source for the purpose of detecting organic contaminants since large and small bodies of water, both above and below ground level are often found to contain various contaminants, and hence are the target of contaminant testing. In addition, water is an inexpensive, safely transportable, non-volatile solvent and can easily be used to wash contaminated soil samples, thus obtaining soluble and partially soluble organic contaminants in aqueous solution.

Quick, inexpensive and accurate qualitative and quantitative tests are needed for the detection of certain organic compounds directly from water or soil. The present invention is an improvement upon known environmental immunoassay tests involving the collection and sampling of water, soil, or air followed by the testing of the water, soil, or air samples, for various contaminants including volatile organic compounds. The improvement according to this invention comprises improving immunoassay accuracy by eliminating all separate sampling steps and testing samples, as collected, on site, for the presence of suspected contaminants. It is contemplated that the air may be tested by dissolving the air sample in a suitable solvent such as, e.g. water or methanol, or absorbing air in activated charcoal that is then extracted with suitable solvent such as, e.g. methanol.

Related immunoassays are disclosed in the commonly assigned and related U.S. patent application, Ser. No. 059,721 filed Jun. 9, 1987 and now abandoned, and its copending, commonly assigned continuation-in-part U.S. application Ser. No. 200,952 filed Jun. 1, 1988. As taught in these U.S. patent applications, many techniques are known for determining the presence of volatile organic compounds in the workplace and the environment, such as gas chromatography, mass spectrophotometry, and high performance liquid chromatography. One drawback to these detection and testing methods is the need to transport the collected samples to an off-site laboratory for further analysis. The vessels containing the samples to be tested must be carefully packaged and shipped to off-site laboratory facilities which in turn raises the overall testing costs. Even the least porous containers suffer the drawback of losing some of the contained volatile materials when the sample containers are opened and prepared for testing such as, e.g., during the preparation of dilutions, or transfer to testing receptacles. The volatile contaminants thus evaporate from the collected sample, inevitably adversely affecting the accuracy of the test result. Certain especially volatile contaminants may leave the sample altogether, resulting in false negative test results indicating a false absence of potentially hazardous compounds at a particular testing site, or drastically understating the true volatile contaminant concentration.

Immunoassays have been commonly used in connection with diagnostic testing, and in conjunction with monitoring drug levels in humans and various animals. However, the use of immunoassay techniques to ascertain the extent to which certain contaminants are present in the environment is relatively new. The use of immunoassays to detect aromatic ring-containing hydrocarbon compounds in soil and aqueous solutions has been disclosed in the aforementioned commonly assigned U.S. patent applications.

The immunoassays according to the invention of this application, are normally assembled in the form of field test kits to be brought directly to the site to be tested. Such tests and test kits are relatively inexpensive, and can be designed to give accurate and immediate results. Soil and aqueous samples suspected of containing various volatile organic contaminants, such as, for example, benzene, toluene, xylene, perchloroethylene and trichloroethylene may thus be tested immediately on-site, before any substantial evaporation of the hazardous volatile contaminant can occur. Therefore, immunoassay testing protocols according to this invention which allow for direct, inexpensive, on-site testing for volatile organic contaminants from samples as collected, which are suspected of containing such contaminants, provide superior overall volatile organic compound detection capabilities.

Further, highly volatile organic compounds, such as benzene, toluene, xylene, perchloroethylene and trichloroethylene begin evaporating to a substantial extent within the first few minutes following collection, from aqueous solutions in which they are only marginally soluble in the first instance. According to heretofore accepted testing methods commonly used in the art, sources suspected of containing the volatile organic compound being tested for are initially sampled, and are often further sampled into aliquots of various volumes in order to preserve the original sample in the event further testing is needed. This aliquot sampling allows the volatile organic compound being assayed for to evaporate from the sample. Further, it has heretofore been customary in the field of immunoassays that extremely small sample volumes when performing an immunologically based test yield the best results. These small volumes usually range between 10 and 500 microliters. In addition, separating such a small volume from the entirety of the sample and transferring this small amount to the ultimate immunoassay reaction vessel, results in another opportunity for volatile organic contaminants to escape from the sample being tested. As a result, a certain percentage of volatile compound evaporation during these aforementioned laboratory procedures is inevitable. Such evaporation, or volatile compound escape invariably affects the final accuracy of the test. Therefore, to conduct an accurate assay for volatile organic compounds, the assay must be initiated as soon as possible after collection.

The degree of volatilization of organic compounds during testing is affected by various ambient conditions during testing such as temperature, solubility of the volatile organic compound in the aqueous solution, and surface area of the sampling receptacle, or testing vessel, etc. While field testing must be conducted at ambient temperatures, the testing receptacles into which the sample is introduced have heretofore been conventionally chilled to temperatures between 2° and 8° C. in a specific attempt to reduce the evaporation of volatiles from the sample. As already discussed, the sample sizes have heretofore been usually restricted and limited to the relatively small volume capacity of the reaction receptacles designed to be used in the accepted testing procedures known in the art. The volume capacity of these receptacles is typically less than approximately 5 mls. It has heretofore been widely believed in the field of immunoassays that sample concentration, rather than sample size, determines sensitivity of the assay. In fact, most prior art immunoassay protocols call for a minimum total test volume in order to measure the analyte at its highest possible concentration when compared to the sample volume. The art has not heretofore appreciated the effect of the sample size, or volume, on the overall accuracy and sensitivity of the assay for volatile compounds. There has to now been concern in the field that the integrity of samples containing volatiles is compromised prior to analysis due to volatile evaporation from the sample solvent. Such volatile evaporation continues to remain a significant cause of inaccurate testing results.

As mentioned previously, the sample volume has oftentimes been limited by design. Conventional practice often calls for use of a sample volume which is equivalent to or less than the volume of the antibody-coated portion of the receptacle device. For example, the use of 4 to 5 ml. cuvettes are common in the immunoassay field. Usually, only the bottom of the cuvette, up to only the 1 ml. mark is coated with antibody. Under these conditions, it is common for samples of not more than about 0.5 to 1.0 ml. to be introduced into the cuvette and assayed. It has now been found according to this invention that, in principle, when assaying for volatile compounds, the volume of the test sample should not be constrained by the amount of antibody coating present at the bottom of the sample vessel nor should the size of the collection vessel deter direct testing in that vessel.

As this invention contemplates, one can coat only the lower portion of a relatively large volume sample collection receptacle with an immunologically coated surface while assaying a total volume of sample that exceeds, by at least about double, the volume that can be contained within the coated portion of the receptacle. Alternatively, if it is cost prohibitive to coat the receptacle with expensive antibody preparation due to the size of the receptacle, then antibody coated insertable insoluble solid-phase devices can be used. Such devices may be of any desired shape or size, but are commonly in the form of wands, sticks, finned sticks, paddles, balls, beads, hoops, loops, meshes, baskets, spiral, etc. The use of such inserts is also contemplated regardless of the area of the surface exposed in the sample collection receptacle. It is further contemplated that the antibody-coated insert devices have a sufficient density to sink to, and remain at the bottom of the collection vessel. When the coated insert device is in the form of a stick, paddle or wand, it is contemplated that the coated portion of the device is completely depressed in the collection vessel so that it comes into contact with, and is held against the bottom of the collection vessel. In this way, the sample volume assayed would cover the antibody coated portion of each insert device to a significant excess.

SUMMARY OF THE INVENTION

The present invention relates to an improved method for detecting volatile organic compounds in soil or aqueous solutions including, but in no way limited to toluene, benzene, xylene, perchloroethylene and trichloroethylene. The essence of this invention is based upon the unexpected discovery that the sensitivity of assays for non-polar organic compounds in aqueous solutions and other polar media, is enhanced by dispensing with sampling via the aliquot approach and testing only an unsegregated lower portion of the entire sample as collected, just as soon after collection as possible. Volatile organic contaminants have been found to display a heightened level of detectability when only a lower layer of sample was tested while in contact with a confining sample overlayer of at least the same volume as the lower layer and preferably several times that volume. When the size of the opening of the collection vessel and hence the sample area exposed to the atmosphere, was kept as small as possible, results are also enhanced. We have found that our immunoassays for the detection and quantification of organic compounds in soil and aqueous solutions and other polar solvent-containing mixtures display a significantly pronounced, unexpected increase in accuracy of detection and quantification when the overall sample size is increased while holding the available evaporation surface area of the sample to a minimum and only the confined lower layer of sample is assayed. This increased detection capability, results in a greatly enhanced immunoassay result.

In addition, it was further discovered that an increase in the total sample size accompanied by assay of only a lower layer sample fraction will also lead to an increased assay sensitivity, whether or not accompanied by concomitant restriction of the exposed surface area at the collection vessel's opening. Therefore, it is believed that the sensitivity increase is somehow due to the increase in sample integrity resulting from the reduced total evaporation of volatile organic materials contained in the sample. In other words, this larger sample appears to retain intact the total volatile organic compound in its lower layer, and also to retain a greater amount of the volatile organic compound being tested for as compared with a small volume of sample, at least when the sample surface area exposed to evaporation is held constant in each instance. This results in an unexpected increase in the overall sensitivity of the immunoassay. It was discovered that such a result occurs even though the concentration of the volatile organic contaminant in both the large and small volume samples was identical at the outset of the testing protocol. While we do not intend to be in any way bound by the theoretical explanations that follow, it is believed that when the reaction vessel is coated essentially only at the very bottom, but is then filled to a level at least twice the volume contained within the antibody coated region, and preferably more, the volatile evaporation begins to take place nearest the top of the sample. The volatile compound will apparently first escape from the sample closest to the surface. The vapor pressure equilibrium then forces some of the volatile compound that had originally been in a lower level of sample to rise through the sample and replace the volatile compound which had left the sample. Eventually this "replacement" volatile compound will also evaporate from the sample. Over a sufficient period of time, even the volatile compound which was present at the bottom of the collection vessel will leave the container. However, the improved assays of the present invention are designed to be completed within a short time period while evaporation of volatile organic compound from the protective sample overlayer is still proceeding. In essence, the protective sample layer in contact with and above the antibody coated level acts as a protective layer which temporarily shields the volatile compound in the assay region (the antibody-coated region) so that it reacts with antibody preferentially over migrating to a higher sample layer.

This invention embraces the further aspects of controlling volatile compound evaporation during an immunoassay procedure including rapid, preferably virtually simultaneous testing and collection of samples, selecting collection/reaction receptacles with restricted available evaporation surface area, filling the collection vessel to at least twice the volume of sample containable within a coated portion of the collection vessel and collecting the sample in such a fashion as to minimize volatile evaporation, e.g. by completely filling the collection vessel with sample and/or capping or sealing the collection vessel immediately after filling. Significantly, it was also discovered, that immediate immunoassay testing in accordance with this invention, before evaporation of the contained organic contaminant occurs, will also result in enhanced detection sensitivity, regardless of the size of the evaporation surface area at the collection vessel's opening.

In quantitative terms, assume that various factors known to affect volatility, (e.g. agitation during sampling, mixing, temperature, relative humidity, ambient vapor pressure, solubility of the contaminant in the solvent, etc.) and available evaporation surface area from which a volatile contaminant in partial solution may evaporate into the atmosphere, are held constant. If a 500 microliter and a 2 milliliter aqueous sample both contain a 10 ppm concentration of a non-polar volatile organic compound such as, for example, benzene, the larger sample contains four times as much mass of benzene as does the smaller sample. If both samples are placed in identical testing receptacles or cuvettes which therefore have the same diameter and internal contour, the same available evaporation surface area results. Under these conditions, the evaporation rate of the volatile compound will be constant. In addition, it should be assumed that the receptacles have each been coated with an amount of antibody such that the antibody-coated surface area covers the same depth of the vessel and has the same antibody concentration per unit volume of sample. Alternatively, if the antibody is instead used to coat a device which is to be inserted in the receptacle, assume the identical device, with the same depth of coating at the lower end and the same antibody concentration per unit volume of sample, is inserted into each receptacle.

In terms of mass of volatile contaminant remaining in the solution, there will be approximately four times the mass of benzene left in the larger sample as compared to the smaller sample. In other words, the constant rate of evaporation affects the larger mass of the volatile organic compound to a reduced degree. This may in part be because of the reduced evaporation surface area per unit volume exposed to the atmosphere and in part because of the greater depth of protective sample layer above and in contact with the sample portion actually assayed. Although the evaporation of the benzene occurs at a constant rate in both samples, since the larger sample begins with a greater mass of benzene in solution, or partial solution, the larger sample retains a greater net amount of organic volatile contaminant over time. This, in turn, has been found to increase the sensitivity of the assay test system.

This unexpectedly enhanced assay sensitivity which coincides with an overall increase in sample size while holding a predetermined volume of about half or less of the total sample the sample portion actually subjected to immunoassay, has led to a change according to the present invention, in the heretofore conventional procedures regarding sample size used to conduct immunoassays and in other detection testing techniques.

When the vessel itself is to be coated, it is contemplated that a suitable receptacle have an opening no larger than about 4 sq. in., and preferably less. In practice, due to the amount of antibody coating required to coat the bottom of a receptacle and the concomitant expense, containers having a maximum volume of about 5 to 100 mls. in the form of test tubes are most commercially feasible and are preferred, although this invention contemplates use of containers that are wider at the bottom and that hold a volume exceeding 25 gallons. In certain cases, the diameter of the container at the opening and below it may be very small, such as 2 to 3 millimeters for a pipette. Alternatively, the diameter of the container opening and its body may be slightly wider; such as 1 to 3 centimeters for test tubes and graduated cylinders. Further, this invention contemplates the use of containers that have necked in openings with body diameters greater than the diameter of the necked in opening, such as common gallon and half-gallon jugs or flasks.

When the receptacle is coated at the bottom with antibody, it is contemplated in one preferred embodiment of the invention that the assay will commence immediately upon contact of the sample with the antibody coating.

In another preferred embodiment, where the antibodies are coated on a solid-phase device to be inserted into the receptacle, the actual assay cannot begin until the coated solid-phase device is brought into contact with the sample. The coated solid-phase device may simply remain at the bottom of the collection vessel in stationary condition, or in another embodiment the coated solid-phase device may be used to agitate the sample.

It is further contemplated that the accuracy of an assay performed in accordance with the process of the present invention will enable one to ascertain and quantify the presence of volatile organic compounds in aqueous solutions at extremely low concentrations in a range as low as about 5 parts per billion or even lower.

As already mentioned, one preferred immunoassay method comprises immersing an insoluble solid-phase device insert into the contaminant-containing sample. In this embodiment, the collection vessel used may have its evaporation surface area defined by a neck narrower than the body of the sample vessel. However, the advantages of the present invention according to this embodiment are realized even if the collection vessel has an opening essentially the same size as the body of the vessel, so long as the reaction time needed for the antibody coated on the insoluble solid-phase device to react with the contaminant is not outrun by the rate of evaporation of contaminant. In other words, the advantages of the present invention are realized, even if the evaporation surface area is relatively unrestricted, so long as large sample volumes are present with a sufficiently deep protective layer of sample covering the bottom layer being assayed and the testing procedures are performed with sufficient dispatch to assure minimal evaporation of volatile organic components from the sample. In this way, this embodiment of the present invention further contemplates that the coated solid-phase device either may be used as a stirrer, or may otherwise be moved evenly throughout the mass of the sample. The movement of the antibody coated solid-phase device can shorten the time it takes to assay the volatile organic contaminant as compared to an assay wherein the device is maintained in a static position since the antibodies more rapidly come into contact with the volatile organic compound contained in the sample.

It is further contemplated that the process of the present invention as already described may be used with immunoassays designed for antibodies which react specifically with only one particular organic contaminant.

It is also contemplated in the present invention that antibodies which are cross-reactive to more than one organic contaminant at one time may be used. The cross-reactive antibodies used in connection with the process of the present invention, are those antibodies harvested from rabbits injected with a conjugate of 6-aminohexyl-p-tolylacetamide with Bovine Serum Albumin (BSA) according to methods well-known in the art. Such cross-reactive antibodies which are able to detect both ring-containing aromatic compounds and aliphatic compounds will shortly, be made the subject of a co-pending U.S. patent application. Immunoassays using these extremely sensitive, cross-reactive antibodies in this invention, allow for the direct sampling of e.g. ground water, soil and air in the form of aqueous or other solutions containing one or more volatile organic compounds, at sample sizes in the order of at least about 0.5 ml. and higher, preferably at least about 1.0 ml. and even more preferably at least about 30 mls. when the antibody-coating (either on the inside walls of the collection vessel or on the inserted coated solid-phase devices) reaches a depth of about 0.25 to about 1.0 ml. of an appropriately scored test tube or graduated cylinder. Larger sample volumes are also contemplated according to this invention. It is recognized that collection receptacles having standard large volume capacities of 1-5 mls. (pipettes), 10-25 mls. (test tubes), 10-500 mls. (graduated cylinders) or 1000 mls. (liter jugs), etc. will be used, due to their widespread availability, in the performance of the present invention.

BRIEF DESCRIPTION OF DRAWINGS

For the purpose of illustrating the invention, there shown a drawing of a form which is presently preferred; it being understood however, that this invention is not limited to precise arrangements and instrumentalities as shown.

DETAILED DESCRIPTION OF THE DRAWING

Figure 1:
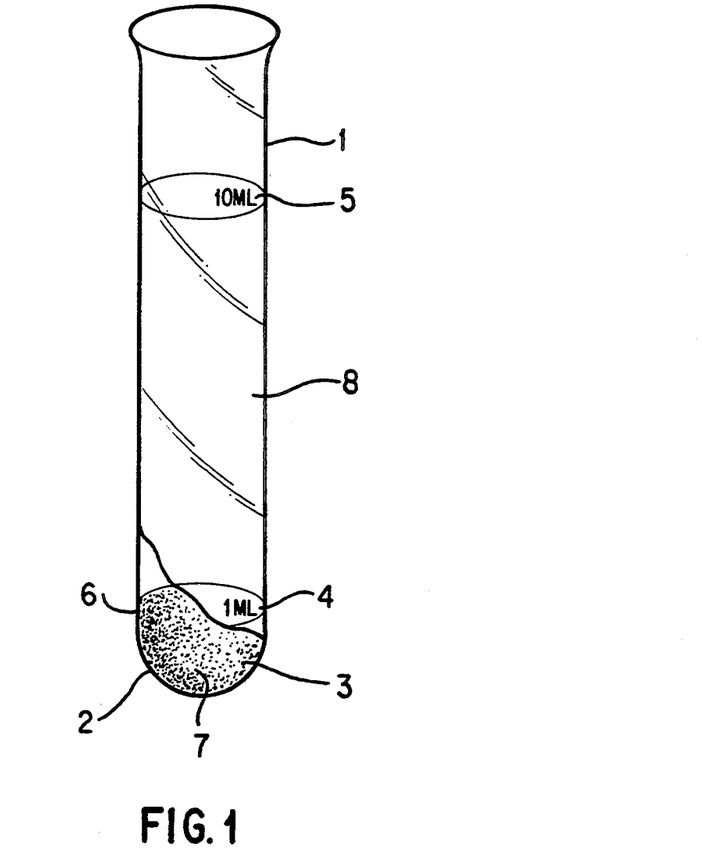
FIG. 1 is a perspective view of an embodiment of a test tribe in accordance with the present invention.

Referring to the drawing in detail, FIG. 1 shows a test tube (1) having a total volume of 15 mls. The bottom of the inside surface (2) of the tube (1) has been covered with an immunologically active coating (3) up to the 1 ml. mark (4) on the tube (1). The tube (1) is further marked at the 10 ml. level (5) as an indication of the sampling level to which the tube is filled with sample. The line (6) indicates the boundary between the lower sample layer (7), which remains at all times in contact with the immunologically active coating (3), and the 9 ml. of sample acting as the protective overlayer (8).

DETAILED DESCRIPTION OF THE INVENTION

The present invention relates to improved immunoassay methods for ascertaining the presence of and quantifying the concentration of volatile organic contaminants present in aqueous and other polar solvent-containing samples obtained from natural water bodies, soil or air. In such immunoassays, the organic contaminant/antibody reaction which occurs can be detected by a variety of methods, using various markers to label the enzyme conjugate, thereby permitting detection of the reaction product. Various methods of quantification or measurement may be used as are well known in the art. Furthermore, immobilization of the antibody will facilitate detection of the contaminant in many cases. It is contemplated that the present invention may be used, e.g., with either competitive or competitive inhibition immunoassays such as are well-known in the field.

It is contemplated that the immunoassay according to the present invention may use monoclonal or polyclonal antibodies, mixtures of the two, and multiple monoclonal or multiple polyclonal antibodies in order to have the broad spectrum screening capabilities needed to detect and quantify the presence of certain volatile organic contaminants, depending upon whether or not one, or more than one, contaminant is being assayed for at any one time.

In the contemplated preferred embodiment of this invention, a known 15 ml. test tube is used as the collecting vessel. The bottom of the tube is coated with antibody by conventional immunoassay methods well-known in the field to a depth of 1 ml. at the bottom end. The sample suspected of containing a volatile contaminant is then introduced into the collecting vessel until the vessel is filled to a preexisting mark representing 10 mls. of volume. The assay is allowed to proceed as in Example 2 below. In this way the layer of sample present above the 1 ml. mark will act as a protective layer for the sample layer surrounded by antibody coating and inhibit the evaporation of volatile compound from the thus trapped lower layer, thus facilitating complete reaction with the antibody coating of the volatile compound in the lowest layer. This enables full detection and quantification of the volatile compound in the lowest layer of the collecting vessel and leads to an enhanced sensitivity level of at least about 5 to 500 ppb of volatile compound.

In another preferred embodiment, the antibody-coated insoluble solid-phase surface may be selected from the group consisting of wands, sticks, finned sticks, paddles, balls, beads, hoops, loops, meshes, baskets, spirals and other immersible objects of convenient shape and size. These devices are sufficiently dense so as to immediately migrate to and remain at the bottom of a collected sample. In a further embodiment, said devices may be placed within the collection vessel prior to the collection of sample.

In still another embodiment, pipettes having a total volume capacity of about 0.5 to 10 mls. have only the lower 10% of the inside walls coated with the antibody. The sample is then drawn out of the source until the pipette is filled to a level of about 20% to 100% capacity of the pipette. In this way, the sample layer containing the volatile compound which is in contact with the antibody coated portion of the pipette will act as a protective layer from which volatile compound preferentially evaporates while the volatile compound layer being assayed reacts with the antibody.

Immunoassay labels that can be used in the practice of the present invention to detect the presence or absence of organic compounds in a sample include enzyme, fluorescent chemiluminescent, and dyed particles as well as radiolabels. In enzyme-linked immunoassays (ELISA), large organic compound(s) can be detected by methods well-known in the art where competition for available immunological binding sites occurs between the organic compound(s) of interest and similar enzyme-labelled compounds. The enzyme activity is typically detected by formation of a colored reaction product, i.e. a colored end-point that may easily be detected by eye or measured by spectroscopic or reflectance means. Several enzymes, including alkaline phosphatase, horseradish peroxidase (HRP) and glucose oxidase have heretofore been coupled to both antigens and antibodies. HRP is commonly used in the field. For visual detection and quantification of the volatile organic compounds contained within the suspect samples, a chromogen will usually comprise a solution of a peroxide and tetramethylbenzidine which manifests a color upon oxidation, the intensity of which can be calibrated to quantify the presence of the volatile organic compounds sought.

The assays of the present invention are applicable to detect any volatile organic contaminant in water, soil, and various polar solvent-containing mixtures. Exemplary volatile organic contaminants include, but are in no way limited to toluene, benzene, xylene, perchloroethylene and trichloroethylene.

As indicated from the examples listed below, the amount of hydrocarbon compound detected in the aqueous or other polar solvent such as e.g. methanol, ethanol, isopropanol, can vary over a wide range. For example, immunoassays in accordance with the process of the present invention are contemplated to detect volatile hydrocarbon compounds down to a range as low as about 5 parts per billion, or even lower.

Monoclonal and polyclonal antibodies to the hydrocarbon compounds sought to be detected in the contaminated samples, for use in the present invention are made using immunization techniques well known in the art. Heterospecific antibodies are particularly useful in conducting tests, according to the present invention, for general or non-specific screening purposes such as, for example detecting the presence of gasoline in a water or soil sample, since a variety of hydrocarbon compounds, together, comprise the liquid hydrocarbon mixture known as gasoline. In addition, several different contaminants often occur in soil or water samples being tested at a particular site or in a particular industrial environment.

One hapten used to obtain the preferred antibody in accordance with the process of the invention, consists of 6-aminohexyl-p-tolylacetamide conjugated to Bovine Serum Albumin (BSA) and injected into a rabbit which is bled after a suitable period of time, usually at least 18 days, followed by extraction of the desired antibody from the blood sample according to methods well known in the art. In accordance with one embodiment of the invention, the resulting antibody is used to coat an insoluble solid phase which is contacted with a sample. This antibody binds toluene and may also bind a number of other organic contaminant compounds such as, but not limited to benzene, as well as a number of aliphatic, straight-chain hydrocarbon compounds. When the insoluble solid-phase antibody coated matrix is a solid phase insert, such insert may be of any shape, size or dimension such as, but is in no way limited to wands, sticks, finned sticks, paddles, balls, beads, hoops, loops, meshes, baskets, spirals, membranes, etc. The sample is collected in a vessel, or receptacle which may or may not have an opening narrower than its main body to minimize evaporation at the surface of the volatile organic compounds contained in the sample. The insoluble solid-phase device is then inserted into the collected sample. The antibody-coated solid-phase device may then remain stationary, or may be moved around throughout the lower layer of the sample so that its volatile organic content may be assayed. The insoluble solid phase matrix itself may, for example, be reacted with certain reactants and "read" to determine and quantify the presence of volatile organic compounds in the collected sample.

It is known that to conduct an accurate assay for volatile organic compounds, the assay must be conducted as soon as possible after collection. The present invention, unlike heretofore used test systems, takes account of this need. Further, the use of an antibody-coated container with an opening no greater than approximately 4 sq. in. where the opening is equal to or less than the widest portion of the collection vessel, serves to additionally inhibit the evaporation of the volatile compound from the sample. The antibody coating on the inside of the collection vessel therefore immediately reacts with the sample. If the antibody is coated on the inside of the collection vessel so as to react with the sample immediately, this, too, aids in overcoming volatility problems.

It is contemplated that a colorimetric or other perceptible and easily determined reaction will occur to signify the presence or absence of volatile organic compounds in the sample. In effect, when the assay system comprising the antibody-coated vessel is lowered into a body of surface, or subterranean water, or filled with a soil sample which is subsequently washed with aqueous solution, the assay system can ascertain the presence or absence of volatile organic compounds in virtually simultaneous fashion. It is therefore contemplated that the assay can be completed in the time it takes to bring, e.g., a soil sample to the surface.

In a further embodiment of the present invention it is contemplated that, an absorptive material such as, e.g. activated charcoal may absorb a volatile organic compound directly from the air and can then be treated with appropriate solvent such e.g. methanol, to remove the volatile compound from the charcoal. The solvent is then immediately assayed in accordance with the invention as already described.

In accordance with the present invention, various labels may be used to further assist in the detection of the hydrocarbon compounds. Such labels may include, but are in no way limited to radioactive labels, enzymes, fluorochromes or luminogens, dye particles and colored latex. Such labels may be attached to antigens or antibodies by methods which are well-known in the art. At present, enzymes are a preferred label. Peroxidases and phosphatases are preferred classes of enzymes and especially preferred are horseradish peroxidase (HRP) and alkaline phosphatase (AP). However, any enzyme which can be conjugated to an antibody, or antigen is contemplated by the process of the present invention. The chromogen contemplated is capable of undergoing a color change in the presence of an enzyme. The chromogen is preferably 3,3',4,5-tetramethylbenzidine (TMB) when horseradish peroxidase is the enzyme.

The following preparation schemes and outlines are presented as further illustrations of the details of the present invention, and only illustrate preferred embodiments of the invention.

Preparation of the Immunogen

The preparation of desired immunogen, (6-aminohexyl-p-tolylacetamide-BSA) according to the preferred embodiment requires the preparation of 6-aminohexyl-p-tolylacetamide by methods known in the art, and the subsequent coupling of the activated compound to the desired protein which in this preferred embodiment is Bovine Serum Albumen (BSA). 6-aminohexyl-p-tolylacetamide is covalently linked to the protein, BSA.

Synthesis Scheme for the
(6-aminohexyl-p-polylacetamide)-BSA Immunogen

The following synthesis is performed to obtain the desired hapten-protein complex used for immunization to produce antibodies by the method already described which is well-known in the art:

The resulting immunogen is used in animal immunization procedures with rabbits or mice in methods which are well known in the art, and are fully disclosed in the commonly assigned U.S. patent applications, Ser. No. 059,721 filed Jun. 9, 1957 and now abandoned, and Ser. No. 200,952 filed Jun. 1, 1988 (which is a continuation-in-part of U.S. Ser. No. 059,721 and currently co-pending). In short, the animals were immunized via injections prepared with Complete Freunds' Adjuvant while subsequent injections (boost) were prepared with incomplete Freunds' Adjuvant. Subsequent bleeding techniques as are well known in the art were then conducted to harvest antibodies from these animals.

Conjugate Labelling Procedure

One preferred embodiment of the invention further contemplates the following labelling procedure for the conjugate which is well-known in the art.

Horseradish Peroxidase Oxidation

Horseradish peroxidase (HRP) in the amount of 4 mg was dissolved in 1 ml of water. The solution was cooled to 4° C. and 200 microliters of cold 0.1 M $NaIO_4$ was added. The solution was then stirred for 90 minutes in the dark at 4° C. Ethylene glycol in the amount of 104 microliters was then added followed by continued stirring for 30 minutes. The resulting solution was then dialyzed overnight at 4° C. against 4 liters of 1 M acetate buffer at pH 4.0.

Coupling the Oxidized Horseradish Peroxidase to 4-methylbenzyl-6-aminohexamide

An amount of 4-methylbenzyl-6-aminohexamide was dissolved in methanol to make a solution in the concentration of 2.85 mg/ml. Next, 175 microliters of the 4-methylbenzyl-6-aminohexamide was added to the oxidized HRP. This was followed, by adding 200 microliters of 0.1 M $Na_2CO_3$, pH 9.5, with the solution then stirred for 2 hours at 4° C. Next, 200 microliters of 4 mg/ml $NaBH_4$ in water was added followed by continued stirring for an additional 30 minutes. The mixture was then dialyzed against 61 ml of 0.01 M phosphate buffer, 0.15 M NaCl at pH 6.0 at 4 overnight. The dialysis was repeated with fresh buffer.

The following examples use the enzyme-labelled conjugate as described above and are presented as further illustrations of the present preferred embodiments of the present invention which are in no sense intended to limit the invention.

EXAMPLE 1

In various embodiments of the present invention, the following stepwise testing protocols were used; as more fully indicated in relation to the ensuing tables of data:

Procedure for Assay with 30 ml. Reaction Volumes with Antibody-Coated "Probes"

1. Mark one tube "S" for sample and the other tube "R" for reference.
2. Add 30 ml. of 4° C. deionized water to each tube.
3. Add 0.5 ml. of 3M tris-(hydroxymethyl) amino methane buffer (pH 7.4) to each tube.
4. Prepare toluene standards in methanol and add 10 microliters. of this standard to the "S" tube and mix. Add 10 microliters of pure methanol to the "R" tube.
5. Add 4 drops of horseradish peroxidase conjugate as disclosed hereinabove to each tube and mix.
6. Insert an antibody coated probe into each tube.
7. Incubate at 4°-10° C. for one minute.
8. Remove probes and wash with water.
9. Insert probes into clean tubes containing 4 drops of urea hydrogen peroxide to each tube as a first color developer, then add 4 drops of tetramethyl benzidine to each tube as a second color developer.
10. Incubate at room temperature for one minute.
11. Remove probes and discard.
12. Add 1 ml. of 1N sulfuric acid to each tube to terminate the reaction.
13. Read the absorbance from the tubes on a spectrophotometer at 450 nm.

EXAMPLE 2

Procedure for Assay with 15 mls. Reaction Volumes

1. Coat two reaction tubes with antibody. Mark one tube "S" for sample and the other tube "R" for reference.
2. Add 15 mls. of cold (4°-10° C.) deionized water to each tube.
3. Add 0.5 ml. of 3M tris-buffer (pH 7.4) to each tube.
4. Add 10 microliters of a 500 ppb standard prepared in methanol to the "S" tube and mix. Add 10 microliters of pure methanol to the "R" tube and mix.
5. Add 4 drops of horseradish peroxidase to each tube and mix.
6. Incubate at 4°-10° C. for one minute.
7. Wash tubes 4 times with deionized water.
8. Add 4 drops of urea hydrogen peroxide to each tube as a first color developer, then add 4 drops of tetramethyl benzidine to each tube as a second color developer.
9. Incubate at room temperature for one minute.
10. Add 1 ml. of 1N sulfuric acid to each tube to terminate the reaction.
11. Read the absorbance from the tubes on a spectrophotometer at 450 nm.

EXAMPLE 3

Procedure for Assays with 0.5, 1.0, and 2.0 mls Reaction Volumes

1. Coat two reaction tubes with the antibody produced from the rabbit as already disclosed. Mark one tube "S" for sample and the other tube "R" for reference.
2. Add appropriate amount of cold (4°-10° C.) deionized water (either 0.5, 1.0 or 2.0 mls.) to each tube.
3. Add 4 drops of 3M tris-buffer (pH 7.4) to each tube.
4. Add 10 microliters of a 10 ppm standard prepared in methanol to the "S" tube and mix. Add 10 microliters of pure methanol to the "R" tube and mix.
5. Add 4 drops of horseradish peroxidase to each tube and mix.
6. Incubate at 4°-10° C. for one minute.
7. Wash tubes 4 times with deionized water.
8. Add 4 drops of urea hydrogen peroxide to each tube as a first color developer, then add 4 drops of tetramethyl benzidine to each tube as a second color developer.
9. Incubate the tubes at room temperature for one minute.
10. Add 1 ml. of 1N sulfuric acid to each tube to terminate the reaction.
11. Read the absorbance from the tubes on a spectrophotometer at 450 nm.

In the following tables, the S/R value is the sample tube (S) to reference tube (R) ratio of absorbance values as read on a spectrophotometer at 450 nanometers. Theoretically, if the sample and reference tubes had the same contents and were run against each other, the tubes and their contents would nave identical absorbance values and the S/R ratio would equal 1.0. However, in practical analytical terms, running two such tubes against each other a number of times and taking readings of each run actually establishes a range which instead only approaches the theoretical value of 1.0. For example, it was determined that for a 0.5 ml sample the S/R value for two tubes containing identical standard contents run at 450 nanometers on a spectrophotometer may range from 0.85 to 1.15, with two standard deviations. This means that when the "S" tube contains an actual sample and is then run against the "R" tube, to positively determine the presence of an organic contaminant, the analyte in the "S" tube must be sufficiently readable such that the value of the "S/R" ratio is lower than 0.85.

By using laboratory methods well-known in the immunochemistry field to carefully establish the relationship between known organic compound concentration in the sample and the S/R ratio absorbance reading on the spectrophotometer, a standard curve, for 0.5 ml. samples containing toluene can be constructed. Through the use of this curve it was further determined that, for 0.5 ml. samples, when the resulting S/R ratio is greater than 0.85, the sample must contain less than 5 parts per million of toluene, or, in other words the S/R ratio is within the range at which positive readings cannot be detected due to the precision limitations on the assay as already described. However, if the S/R ratio produces a value that is between 0.50 and 0.85, it was determined that the sample contains 5 to 10 parts per million of toluene. Finally, if the S/R ratio produces a value that is less than 0.50, it was determined that the toluene concentration of the sample is greater than 10 parts per million.

While the standard curve derived as described above, and the following data presented were specifically evaluated with reference to the standard curve for toluene presence in a 0.5 ml. sample, it is clear that similar curves can be created for other volatile organic compounds and mixtures thereof, as well as for various other sample volumes, using the technique described. Moreover, examples of such volatile organic compounds include but are in no way limited to benzene, xylene, perchloroethylene, trichloroethylene and mixtures including volatile organic compounds such as, for example, gasoline.

The data in Table 1 represents the assay sensitivity differences of aqueous toluene as the sample sizes (volumes) are progressively increased. The protocol as described in Example 3 when 0.5, 1.0 and 1.5 mls. samples are tested was followed to obtain the results stated. In Table 1, "PPM" is parts per million of toluene in solution, "S" is the sample tube, and "R" is the reference tube. The "Observed % Increased Sensitivity" shows the enhanced sensitivity of the 1.0 ml sample as compared to the 0.5 ml. sample when the concentration of toluene in the sample is held constant (5 ppm). This increase, therefore, represents the change in S/R ratio value that is observed as the volume is increased from the 0.5 ml. "baseline", on which the toluene standard curve is based. All tests were run on the spectrophotometer at an absorbance setting of 450 nanometers.

TABLE 1

| | Toluene | | |
|---|---|---|---|
| Sample Vol. (ml.) | PPM | S/R Ratio | Observed % Increased Sensitivity |
| 0.5 | 5 | 0.770 | 100 |
| 1.0 | 5 | 0.550 | 142 |
| 1.5 | 5 | 0.378 | 207 |

The data in Table 1 shows that as the overall volume of aqueous toluene samples is doubled and tripled, the immunoassy S/R ratio dropped significantly in value, resulting in an observed sensitivity increase, even though the actual concentration of the toluene per unit volume remained constant throughout.

The comparative data in Table 2 further shows the immunoassay sensitivity differences of aqueous toluene as the volume of the sample is increased. When the volume of the toluene sample was held to 0.5 ml, the immunoassay was only able to detect the toluene at approximately a 2 PPM concentration. However, when the volume was increased to 15 ml samples, the toluene was detectable at concentrations as low as 0.167 PPM. Similar data was collected for the detection of benzene in aqueous solution.

All reagents were used, and the assays were performed at ambient conditions. The "S" and "R" tubes were stored prior to the assay in ice water and therefore maintained at the 2°–8° C. range. The protocol used is the protocol described in Examples 2 or 3 depending upon the volume of the sample tested. In Table 2, "PPM" is parts per million of toluene in solution, "S" is the sample tube, "R" is reference tube, "S/R" is the sample to reference ratio as already described, and "n" is the number of test runs made on each sample. All tests were run on the spectrophotometer at an absorbance setting of 450 nanometers. The "Range" column reflects the "high" and "low" values from the 3 runs made.

TABLE 2

| Analyte | Assay Vol (ml) | PPM Analyte | S/R Ratio | n | Range |
|---|---|---|---|---|---|
| Toluene | 0.5 | 0.2 | 0.972 | 3 | 0.79–1.16 |
| Toluene | 0.5 | 0.5 | 1.090 | 3 | 1.00–1.18 |
| Toluene | 0.5 | 1 | 1.040 | 3 | 1.03–1.05 |
| Toluene | 0.5 | 2 | 0.888 | 3 | 0.87–0.91 |
| Toluene | 15 | 0.067 | 0.966 | 3 | 0.87–1.06 |
| Toluene | 15 | 0.167 | 0.732 | 3 | 0.69–0.77 |
| Toluene | 15 | 0.333 | 0.685 | 3 | 0.66–0.71 |
| Toluene | 15 | 0.670 | 0.568 | 3 | 0.41–0.73 |

The data in Table 2 shows that when the volume of toluene is increased significantly (15 mls. as compared to 0.5 ml.), the observed sensitivity of the assay is apparently markedly increased.

The comparative data in Table 3 shows the immunoassay sensitivity differences of aqueous toluene as the volume of the sample is increased. All reagents were used, and the assays were performed at ambient conditions. The "S" and "R" tubes were stored prior to the assay in ice water and therefore maintained at the 2°–8° C. range. The protocol used, is basically the protocol described in Examples 2 or 3 depending upon the sample volumes used. In Table 3, "PPM" is parts per million of tolune in solution, "S" is the sample tube, "R" is reference tube, "S/R" is the sample to reference ratio as already explained, and "n" is the number of test runs made on each sample. All tests were run on the spectrophotometer at an absorbance setting of 450 nanometers.

TABLE 3

| | | | Toluene | | | |
|---|---|---|---|---|---|---|
| Volatile Cmpd. | PPM | Sample Vol. | (S) 450 nm | (R) 450 nm | S/R | n |
| Tol. | 10 | 0.5 ml | 0.282 | 0.623 | 0.453 | |
| Tol. | 10 | 0.5 ml | 0.297 | 0.618 | 0.481 | |
| Tol. | 10 | 0.5 ml | 0.347 | 0.744 | 0.466 | |
| | | | | | mean = 0.467 | 3 |
| Tol. | 2 | 0.5 ml | 0.464 | 0.828 | 0.560 | |
| Tol. | 2 | 0.5 ml | 0.533 | 0.789 | 0.676 | |
| Tol. | 2 | 0.5 ml | 0.550 | 0.658 | 0.835 | |
| | | | | | mean = 0.690 | 3 |
| Tol. | 1 | 0.5 ml | 0.336 | 0.398 | 0.844 | |
| Tol. | 1 | 0.5 ml | 0.300 | 0.461 | 0.651 | |
| Tol. | 1 | 0.5 ml | 0.271 | 0.373 | 0.727 | |
| | | | | | mean = 0.744 | 3 |
| Tol. | 1 | 1.0 ml | 0.192 | 0.288 | 0.667 | |
| Tol. | 1 | 1.0 ml | 0.181 | 0.259 | 0.699 | |
| Tol. | 1 | 1.0 ml | 0.144 | 0.237 | 0.608 | |
| | | | | | mean = 0.658 | 3 |
| Tol. | 0.5 | 1.0 ml | 0.219 | 0.326 | 0.672 | |
| Tol. | 0.5 | 1.0 ml | 0.182 | 0.260 | 0.700 | |
| Tol. | 0.5 | 1.0 ml | 0.230 | 0.250 | 0.920 | |
| | | | | | mean = 0.764 | 3 |
| Tol. | 0.25 | 1.0 ml | 0.160 | 0.227 | 0.705 | |
| Tol. | 0.25 | 1.0 ml | 0.184 | 0.221 | 0.833 | |
| Tol. | 0.25 | 1.0 ml | 0.199 | 0.210 | 0.948 | 3 |
| | | | | | mean = 0.829 | |
| Tol. | 0.5 | 2.0 ml | 0.123 | 0.159 | 0.774 | |
| Tol. | 0.5 | 2.0 ml | 0.166 | 0.220 | 0.755 | |
| Tol. | 0.5 | 2.0 ml | 0.207 | 0.293 | 0.706 | |
| | | | | | mean = 0.745 | 3 |
| Tol. | 0.25 | 2.0 ml | 0.199 | 0.318 | 0.626 | |
| Tol. | 0.25 | 2.0 ml | 0.199 | 0.293 | 0.679 | |
| Tol. | 0.25 | 2.0 ml | 0.203 | 0.278 | 0.730 | |
| | | | | | mean = 0.678 | 3 |
| Tol. | 0.25 | 4.0 ml | 0.155 | 0.158 | 0.981 | |
| Tol. | 0.25 | 4.0 ml | 0.109 | 0.123 | 0.886 | |
| Tol. | 0.25 | 4.0 ml | 0.130 | 0.170 | 0.765 | |
| | | | | | mean = 0.877 | 3 |
| Tol: | 0.333 | 15 ml | 0.351 | 0.484 | 0.725 | |

TABLE 3-continued

| Volatile Cmpd. | PPM | Sample Vol. | Toluene (S) 450 nm | (R) 450 nm | S/R | n |
|---|---|---|---|---|---|---|
| Tol. | 0.333 | 15 ml | 0.331 | 0.480 | 0.690 | |
| Tol. | 0.333 | 15 ml | 0.439 | 0.537 | 0.818 | |
| | | | | | mean = 0.744 | 3 |
| Tol. | 0.167 | 15 ml | 0.113 | 0.236 | 0.479 | |
| Tol. | 0.167 | 15 ml | 0.594 | 0.655 | 0.907 | |
| Tol. | 0.167 | 15 ml | 0.506 | 0.458 | 1.100 | |
| Tol. | 0.167 | 15 ml | 0.650 | 0.742 | 0.876 | |
| Tol. | 0.167 | 15 ml | 0.602 | 0.739 | 0.815 | |
| | | | | | mean = 0.835 | 5 |

While the present invention has been described with respect to its various and preferred embodiments, it is not intended to limit such invention by the description here given. Various alternative ways of proceeding and various embodiments not specifically described will be readily apparent to those skilled in the art, and it is intended that they be embraced within the scope of the invention, insofar as the appended claims may permit.

What is claimed is:

1. An immunoassay method to detect a volatile organic compound analyte present in a sample of non-volatile polar solvent, which analyte is present at a concentration of at least between about 5 parts per billion and about 10 parts per million, said method comprising the steps of:
   (a) collecting a sample in a vessel, which vessel comprises
      (i) a lower portion having volume capacity of at least about 0.5 milliliters and having an antibody specific for said analyte immobilized on the inner surface of the lower portion of the vessel, and
      (ii) an upper portion which is not immunologically reactive with said analyte,
      wherein the total volume of said sample is at least twice the volume of the volume of sample which is contained in the lower portion of the vessel;
   (b) adding to said sample a conjugate between a detectable label and an organic compound for which the immobilized antibody is specific;
   (c) allowing any of said analyte in said sample for which said antibody is specific to bind to said immobilized antibody in said lower portion of said vessel in the presence of said conjugate, under conditions in which said conjugate and said analyte in the sample compete for binding with said antibody;
   (d) detecting the binding of said detectable label to said lower portion of said vessel thereby detecting said volatile organic compound analyte in said sample.

2. The method of claim 1 wherein the total volume of said sample is between about twice and about thirty times the volume of sample which is contained in the lower portion of the vessel.

3. The method of claim 1 wherein said analyte is selected from the group consisting of benzene, toluene, xylene, perchloroethylene and trichloroethylene, or a mixture of any two or more thereof.

4. The method of claim 1 wherein said total sample volume is at least about 15 milliliters.

5. The method of claim 4 wherein said total sample volume is between about 30 milliliters and about 60 milliliters.

6. The method of claim 1, wherein said sample is obtained from soil.

7. The method of claim 1 wherein said sample is obtained from air by
   (a) absorptive filtering of air with an absorptive filtering substance; and
   (b) extracting said absorptive filtering substance with a polar solvent.

8. The method of claim 7, wherein said polar solvent is selected from the group consisting of methanol, ethanol and isopropanol.

9. The method of claim 7 wherein said absorptive filtering substance is activated charcoal.

10. An immunoassay method to detect a volatile organic compound analyte present in a sample of non-volatile polar solvent, which analyte is present at a concentration of between about 5 parts per billion and about 10 parts per million, said method comprising the steps of:
    (a) collecting a sample in a vessel, which vessel comprises
       (i) a lower portion having a volume capacity of at least about 0.5 milliliters and having inserted therein a removable solid phase device, said device having a surface, on all or part of which surface is immobilized an antibody specific for said analyte, and
       (ii) an upper portion which is not immunologically reactive with said analyte,
       wherein the total volume of said sample is at least twice the volume of the volume of sample which is contained in the lower portion of the vessel;
    (b) adding to said sample and said device a conjugate between a detectable label and an organic compound for which the immobilized antibody is specific;
    (c) allowing any of said analyte in said sample for which said antibody is specific to bind to said antibody immobilized on said device in the presence of said conjugate, under conditions in which said conjugate and said analyte in the sample compete for binding with said antibody;
    (d) detecting the binding of said detectable label to said device thereby detecting said volatile organic compound analyte in said sample.

11. The method of claim 10 wherein said analyte is selected from the group consisting of benzene, toluene, xylene, perchloroethylene and trichloroethylene, or a mixture of any two or more thereof.

12. The method of claim 10, wherein said sample is obtained from soil.

13. The method of claim 10 wherein said sample is obtained from air by
    (a) absorptive filtering of air with an absorptive filtering substance; and
    (b) extracting said absorptive filtering substance with a polar solvent.

14. The method of claim 13, wherein said polar solvent is selected from the group consisting of methanol, ethanol and isopropanol.

15. The method of claim 13 wherein said absorptive filtering substance is activated charcoal.

* * * * *